US010493467B2

(12) United States Patent
Lundquist et al.

(10) Patent No.: US 10,493,467 B2
(45) Date of Patent: Dec. 3, 2019

(54) CENTRIFUGE AND METHOD OF CENTRIFUGING A BLOOD SAMPLE (71) Applicant: REAPPLIX APS, Birkerod (DK)

(72) Inventors: Rasmus Lundquist, Bronshoj (DK); Neils Erik Holm, Birkerod (DK)

(73) Assignee: REAPPLIX APS (DK)

( * ) Notice: Subject to any disclaimer, the term of this patent is extended or adjusted under 35 U.S.C. 154(b) by 0 days.

(21) Appl. No.: 15/504,370

(22) PCT Filed: Aug. 19, 2015

(86) PCT No.: PCT/EP2015/069067
§ 371 (c)(1),
(2) Date: Feb. 16, 2017

(87) PCT Pub. No.: WO2016/026901
PCT Pub. Date: Feb. 25, 2016

(65) Prior Publication Data
US 2017/0232452 A1    Aug. 17, 2017

(30) Foreign Application Priority Data
Aug. 19, 2014 (EP) .................................. 14181377

(51) Int. Cl.
B04B 5/04     (2006.01)
A61M 1/36    (2006.01)
B04B 13/00   (2006.01)

(52) U.S. Cl.
CPC ......... B04B 5/0421 (2013.01); *A61M 1/3693* (2013.01); *B04B 13/00* (2013.01); *A61M 2205/3306* (2013.01); *B04B 2013/006* (2013.01)

(58) Field of Classification Search
CPC ..... B04B 5/0414; B04B 5/0421; B04B 13/00; B04B 2013/006; A61M 1/3693; A61M 2205/3306
See application file for complete search history.

(56) References Cited

U.S. PATENT DOCUMENTS 3,674,198 A *  7/1972  Eberle ..................... B04B 5/04
                                                          211/74
4,766,083 A    8/1988  Miyashita et al.
(Continued)

FOREIGN PATENT DOCUMENTS

WO     200132289 A1    5/2001
WO    2008121120 A1   10/2008

OTHER PUBLICATIONS

International Search Authority International Search Report—PCT/EP2015/069067, dated Feb. 25, 2016.
(Continued)

Primary Examiner — Timothy C Cleveland
(74) Attorney, Agent, or Firm — Luedeka Neely Group, PC (57) ABSTRACT A centrifuge comprising a rotor having a rotational axis, at least one receptacle for a blood sample container, controller means for controlling the rotational speed of the rotor, at least one optical transmitter for transmitting an optical signal, at least one optical receiver for registering the amplitude of the optical signal, where the optical signal is configured to pass through the blood sample container where the optical receiver detects the amplitude of the optical signal when it is directed through the blood sample container, where the amplitude of the optical signal reflects the translucency of the blood sample, where the controller means is configured to discontinue the rotational movement of the rotor when the amplitude of the optical signal over (Continued)

time has fulfilled a predefined pattern indicating that at least the fibrin compression phase of the blood sample is started.

19 Claims, 3 Drawing Sheets

(56) References Cited

U.S. PATENT DOCUMENTS

| | | |
|---|---|---|
| 4,777,141 A | 10/1988 | Calzi et al. |
| 7,438,679 B2 | 10/2008 | Hlavinka et al. |
| 8,236,184 B2 | 8/2012 | Holmes et al. |
| 8,535,210 B2 | 9/2013 | Kolenbrander et al. |
| 8,980,301 B2 | 3/2015 | Lundquist et al. |
| 2013/0140226 A1 | 6/2013 | Lundquist et al. |
| 2014/0057771 A1 | 2/2014 | Case et al. |

OTHER PUBLICATIONS

International Search Authority Written Opinion—PCT/EP2015/069067, dated Jul. 8, 2016.

* cited by examiner

CENTRIFUGE AND METHOD OF CENTRIFUGING A BLOOD SAMPLE

RELATED APPLICATION

This application claims priority to PCT/EP2015/069067, filed Aug. 19, 2015.

FIELD OF THE INVENTION

A centrifuge and a method of controlling a centrifuge comprising a rotor having a rotational axis, at least one receptacle for a blood sample container, controller means for controlling the rotational speed of the rotor, at least one optical transmitter for transmitting an optical signal, at least one optical receiver for registering the amplitude of the optical signal.

BACKGROUND

In modern medicine there is an increased tendency in utilizing elements from blood in the treatment of ailments or for diagnostic use. One method of extracting elements from blood such as thrombocytes (platelets), leukocytes (white blood cells) or blood plasma is by fractionating whole blood by placing a container of whole blood in a centrifuge where the blood becomes separated into its component parts.

The component parts may be utilized for specific treatment or diagnostic purposes for the human body, where the specific components may be administered to a patient that might need a dosage of thrombocytes, in case that a patient does not have enough thrombocytes in case of a haemorrhage. Another use for the component parts of whole blood may e.g. be in wound treatment, where the whole blood may be introduced into a container where the blood is induced to coagulate and where upon a specific centrifugation regime the components of the whole blood have been concentrated into a blood product.

WO 2010/020254 discloses how to prepare a multilayered blood product by centrifugation of blood, where the blood is placed in a container and the coagulation of the blood is activated during or after placing the blood in the container. During the centrifugation, the components of the blood are separated from each other and produce a three-layered blood product, which in sequential order comprises a first layer, which substantially comprises fibrin, a second intermediate layer, which substantially comprises thrombocytes, and a third layer, which substantially comprises leukocytes.

WO 2012/037942 discloses a container to be used for preparing a multi-layered blood product by centrifugation, where said container comprises a filling opening as well as a filter device which is slidable inside the container. The filter device comprises a planar mesh and a supporting buoyancy body, where the filter device is adapted to collect the multi-layered blood product on or above the mesh.

In WO 2010/020254 and WO 2012/037942 there is a requirement that the whole blood and/or the container holding the whole blood has to be centrifuged a certain amount of time at a certain speed in order to ensure that the blood product has been formed inside the container.

However, as one of the important factors for the provision of the blood product is the coagulation of the whole blood inside the container, it has been observed that the coagulation time of whole blood may vary significantly from one donor to another. This variation in coagulation time affects the centrifugation process of the container holding the whole blood, as the preparation time of the blood product may differ considerably for two different blood donors. It is also to be recognised that other factors, such as age, medicaments, diet and health of the donor can affect the preparation time of the blood product using a centrifuge.

Thus, the medical professionals that are preparing a blood product, such as the blood product disclosed in WO 2010/020254, do not have any methods for determining the exact amount of time that is necessary at a certain speed to ensure that the blood product is ready for use for wound healing, prior to the centrifugation process.

The centrifugation process of the blood product is often performed using a benchtop or a table centrifuge that is provided with a rotor that rotates along a vertical axis, where the containers are arranged in a radial direction away from the rotational axis. The containers are often either fixed at a certain angle, or they may be arranged to be positioned at one angle to the rotational axis when the rotor is stationary and to rotate in a direction towards a plane that is perpendicular to the rotational axis when the rotor has been accelerated into rotational motion, i.e. swinging head centrifuges or swing-out (buckets) centrifuges. Such rotational movement of the container ensures that he centrifugal force during centrifugation may be directed along the longitudinal axis of the container, ensuring that the particles density of the particles inside the whole blood is in a sequential order, where the particles having a higher density is at a distal end of the container, while the particles having smaller densities are concentrated at a more proximal position in the container. The terms proximal and distal defined in relation to the rotational axis of the centrifuge, where the distal end of the container is the part of the container that is arranged farther away from the rotational axis during centrifugation, while the proximal end is arranged closed to the rotational axis.

For safety reasons, a benchtop or a table centrifuge is provided with a lid, so that the rotating motion of the rotor cannot injure or harm any persons that are in the vicinity of the centrifuge during operation. Thus, this often means that the blood samples or the whole blood inside the container cannot be inspected during centrifugation, as there is no direct visual access to the content of the container. Furthermore, as the centrifuges can operate at a rotational speed that may be up to 4000 RPM, 8000 RPM or more, i.e. approximately 66-132 revolutions per second or more, it may be difficult or even impossible to visualise the state of the contents of the container during rotation with the bare eyes, even if there would be direct visual access to the contents of the container.

Furthermore, as coagulation occurs over a certain period of time, where the termination of the coagulation is indicated by the lack of change in optical density, the process has to be observed continuously during the process in order to get the optimal result of the coagulation process.

Thus, the medical professionals preparing a blood product do not have any methods or tools to recognise when the centrifugal process of the container has been carried out enough to prepare the blood product sufficiently for use. Thus, the medical professionals have tried to figure out an amount of time that is sufficient for most users, and apply this qualified guessed amount of time to the centrifugal process. As an example, if the predetermined amount of time is 10 minutes, this amount of time may be sufficient for some donors, while for other donors the blood has to be reintroduced to the centrifugal process after removing the container from the centrifuge and visually inspecting the contents. For some donors, the blood product may be ready within 2-5 minutes, while for other donors the blood product may be ready within 15-20 minutes or even more, of the initial centrifugation.

Thus, if it is necessary to prepare multiple blood products for the wound treatment of a donor, each minute of wasted centrifugation and/or visual inspection may be multiplied by the amount of products to be prepared by subsequent centrifugation processes. Thus, there is a need to increase the efficiency of the centrifugal process.

GENERAL DESCRIPTION

In accordance with the invention, there is provided a centrifuge comprising a rotor having a rotational axis, at least one receptacle for a blood sample container having a gravitational axis, where the receptacle comprises a top end for receiving a blood sample container and a bottom end for holding the blood sample container, where the receptacle is in a position that is at an angle to the rotational axis of the centrifuge, where the centrifugal force extends from the top end of the receptacle towards the bottom end of the receptacle, controller means for controlling the rotational speed of the rotor, at least one optical transmitter for transmitting an optical signal in a direction that is at an angle to the gravitational axis of the receptacle and through an upper phase and/or the plasma of a blood sample in the blood sample container, at least one optical receiver for registering the amplitude of the optical signal, where the optical signal is configured to be directed towards the blood sample container where the optical receiver detects the amplitude of the optical signal, where the amplitude of the optical signal reflects the translucency of the upper phase and/or the plasma of the blood sample, where the controller means is configured to discontinue the rotational movement of the rotor when the amplitude of the optical signal over time has fulfilled a predefined pattern, indicating that at least the fibrin polymerisation phase of the blood plasma is started.

The measurement of the translucency of blood is a relative factor, depending on the choice of optical transmitters and optical receivers, as well as the material of a blood sample container. Thus, in relation to the present invention, the amplitude of optical signal is considered as a representation of a relative translucency where the measurements are adapted to detect the change in translucency over time of the blood sample. The optical transmitter may be a LED based transmitter, a laser diode, where a light at a suitable wavelength may be directionally emitted towards an optical receiver. The optical receiver may be a photodetector, such as p-n photodiodes, p-i-n photodiode, avalanche photodiode or any type of photodetector that is capable of registering and differentiating the amplitude of the received light.

The centrifuge may be of the kind where the receptacle may be adapted to move from a position where the gravitational axis is substantially parallel to the rotational axis of the centrifuge to a position that is substantially perpendicular to the rotational axis of the centrifuge. The centrifuge may thus be a bucket centrifuge having a swinging bucket (receptacle) or may be a fixed angled centrifuge, where the bucket (receptacle) may be fixed at a certain angle relative to the rotational axis of the centrifuge.

The angle of the receptacle in relation to the rotational axis of the centrifuge may be between 30° and 90°. It has been shown that a preferred method of centrifuging may be where the receptacle is at a 90° angle relative to the rotational axis, or where it is substantially perpendicular to the rotational axis. Some centrifuges may have a receptacle where the receptacle is at a fixed angle, where the angle may be anywhere between 30° and 90°.

The centrifuge in accordance with the present invention may be a rotational centrifuge that provides centrifugal force for the sedimentation of whole blood by increasing the gravitational force that is applied to a container comprising whole blood. The rotor of the centrifuge may be adapted to put the receptacle in rotation around a fixed axis, so that the centrifugal force is applied perpendicular to the fixed axis. The receptacle may be hinged inside the centrifuge, so that the receptacle is in a substantially vertical position (parallel to the fixed axis) when arrested and during centrifugation the receptacle will tilt towards a substantially horizontal position (perpendicular to the fixed axis). Thus the longitudinal axis of the receptacle and/or the blood sample container may be substantially perpendicular to the fixed axis during centrifugation, so that the centrifugal force is applied in a direction parallel to the longitudinal axis of the receptacle and/or the blood sample container. Alternatively, the centrifugal force may be applied in a direction that is at an angle to the longitudinal axis of the blood sample container, where the angle may be between about 1° and 60° degrees.

Thus, the centrifugal force may be seen as being in a direction that extends in a direction away from the rotational axis of the centrifuge so that the gravitational force first intersects the top of the blood sample container and/or the receptacle and subsequently intersects the bottom of the blood sample container and/or the receptacle. This means that the top of the receptacle/container is closer to the centrifugal axis of the centrifuge than the bottom of the container, which means that the centrifugal force forces the blood separation in a direction from the top of the container/receptacle towards the bottom of the container/receptacle. Hence, the gravitational field, which is applied by the centrifuge to the receptacle and/or the container is lower in the area of the container/receptacle that is closer to the rotational axis, i.e. in the top end of the container/receptacle, than it is in the area of the container/receptacle that is distant to the rotational axis, i.e. in the bottom end of the container/receptacle. The gravitational field may be calculated using the following formula $$RCF = 1.118 x R x \left(\frac{RPM}{1000}\right)^2$$

where RCF is the rotational centrifugal force, R is the radius of rotation (measured in millimetres) and RPM is the rotational speed of the centrifuge.

Within the meaning of the present invention, the upper part of the container may be a part of the container that is proximal to the fixed axis of the centrifuge during centrifugation while the lower part of the container is the part of the container that is distal to the fixed axis of the centrifuge.

During centrifugation of the whole blood into a blood product, the phases of the blood fractionation may comprise the following phases when the blood sample is being centrifuged:

Separation of blood. This may be seen as the initial separation of blood into its components, where the whole blood separates into a clear solution of blood plasma in the upper part of the container, an intermittent part of a buffy coat comprising leucocytes and platelets, and erythrocytes at the bottom of the container as the erythrocytes have a higher density than leucocytes and the platelets. In this phase, the blood plasma comprises fibrinogen monomers. This separation may be seen in three phases where the separation may be seen as the separation of leukocytes, separation of platelets Fibrin polymerisation, where the fibrinogen monomers polymerize end to end to form protofibrils which associate laterally to form fibrin fibres. The fibrin polymerisation phase in the blood plasma causes the translucency of the blood plasma to decrease as the fibrin is formed.

Fibrin compression, when the fibrin polymerisation is completed, the fibrin fibres inside the plasma begin to compress on top of the thrombocytes due to the centrifugation, and the translucency of the blood plasma begins to increase.

Clearing of other plasma components, in this phase, the fibrin compression has been completed and other components in the plasma begin concentrate causing the translucency of the blood plasma to increase even further. The other components may include particles, cells and molecules, such as fat, fibrin, fibrinogen, or any other components that are in the blood plasma and will clear during the centrifugation. The separation of blood may be seen as a process where the separation is intended to separate different parts of the blood into separate areas of the container. The separation may be the separation of erythrocytes, the separation of leucocytes and the separation of platelets, where the three separation phases of the process may be identified using measurements utilizing optical signals that are directed through parts of the whole blood.

Each of the above phases of the blood fractioning can be recognized using a measurement of the translucency of the blood plasma, where certain changes in the translucency pattern during substantially constant centrifugation process indicates the shift from one phase to its subsequent phase.

The optical transmitter may be adapted to transmit the optical signal, where the optical receiver is adapted to measure the amplitude of the signal on a predefined scale. The optical signal passes through the blood sample container and if the optical signal is intersected by components in the liquid parts optical signal will diffuse due to the intersection, and only parts of the optical signal will pass through the container to be received by the optical receiver, and the amplitude of the signal will be reduced on the predefined scale. As the optical signal is registered over time it is possible to monitor whether the clarity of the liquid inside the container is constant, increasing or decreasing relative to the predefined scale.

The controller means may be adapted to receive an input from the optical receiver, so that the amplitude of the optical signal may be utilized to control the rotational speed of the centrifuge. The controller means may comprise a signal comparator, so that when a certain threshold, pattern or tendency of the signal is observed by the controller means, the controller means will adjust the rotational speed of the centrifuge by controlling the current or the voltage of the electrical signal that is sent to the motor of the centrifuge. The controller means may be in the form of a microprocessor, microcontroller, being capable of receiving electrical signals transmitted from the optical receiver, processing the signals received and performing certain operations based on the electrical signals received by sending out output signals to control the rotational movement of the centrifuge.

The centrifuge may be configured so that the optical signal is directed to pass through an upper part of the container, so that the optical signal passes through the blood plasma during the initial separation of blood. This means that the amplitude of the optical signal is capable of registering when the components (buffy coat and erythrocytes) in the whole blood are forced towards the bottom of the container due to the centrifugal forces during centrifugation. Thus, by transmitting the optical signal into an upper part of the container the amplitude difference between the clear blood plasma and the whole blood is maximized, allowing maximal variation in the amplitude of the optical signal. Should the optical signal be transmitted through the lower part of the container, the transmission through the whole blood would commence through an opaque part of the blood sample and the transmission amplitude would decrease during the initial blood separation phase, as the buffy coat and the erythrocytes would shift towards the bottom of the container causing the liquid to become more opaque. Thus the amplitude variation would be reduced, which could cause a reduced reliability of the measurements compared to a measurement that passes through the upper part. Such a measurement could be performed, and a pattern for the separate phases could be identified, but the reliability of a measurement in the upper part is seen as being greater, as the variation in the opaqueness and/or transparency of the liquid is greater.

Alternatively, the optical signal may be a light source that illuminates the container, where the optical receiver may be in the form of a camera that is capable of registering the amplitude of the light reflecting off the container, so that when the liquid is translucent the amplitude of the optical signal received by the camera is low, where the optical signal increases when the translucency of the plasma is reduced. Thus, in such a measurement the amplitude of the optical signal may be inverted in view of in an embodiment where the optical signal passes through the container. Thus the pattern of the amplitude may be obtained by image analysis or image processing of the signal obtained by the camera, such as feature extraction. The camera may obtain continuous or discrete images that are fed into a pattern recognition software that may be part of the controller or working in conjunction with the controller.

Thus, by continuously registering the amplitude of the optical signal over time it is possible to monitor the centrifugation process in order to assess in what state the blood sample is in at a given moment in time. When the signal has followed a predefined pattern it is possible to determine that the blood sample is in a desired state, allowing the blood product to be collected from the blood sample container. Thus, the centrifugation may be stopped when the blood sample has reached its desired phase of blood fractionation ensuring that the centrifugation is not discontinued prior to the desired phase or that the centrifugation is not carried out longer than necessary.

The predefined pattern may be defined by analysing the signals from several individual patients, where it is possible by trial and error to find similar patterns in the optical detection which indicates that the at least fibrin compression phase is started.

Furthermore, it may be possible to monitor the signal live on a graph, which allows the professional to analyse the signal to find the correct time when the coagulation and/or blood fractioning has reached a level that is enough to form a blood production.

The centrifugation may be continued beyond the preliminary part of the fibrin compression phase, in order to ensure that all the fibrin has been compressed in the lower part of the container. The amplitude of the optical signal in the upper part of the container will decrease during fibrogen polymerisation phase, as the fibrogen molecules bond with each other and cause the plasma to be more opaque during the polymerisation phase. Subsequently, when the fibrogen polymerisation is finished, the fibrin begins to compress in the lower part of the container, causing the amplitude of the optical signal to increase during the fibrin compression phase, as the polymeric fibrogen (fibrin) is cleared from the blood plasma. The centrifugation may further be continued into the clearing of plasma components phase which supersedes the fibrin compression phase, as the amplitude of the optical signal is increased even further as the components in the plasma move towards the bottom of the container due to the centrifugal force, or where the components may move towards the top of the container due to their density, e.g. where fat components float towards the surface of the plasma.

In one embodiment, the predefined pattern may indicate that a fibrin polymerisation phase is started. The fibrin polymerisation phase may be seen as the phase where the composition of a blood product is beginning to become ready. The fibrin polymerisation allows the fibrin to be compacted in a subsequent phase, so that the remaining components, thrombocytes and leukocytes, may be adhered to the fibrin. The fibrin polymerisation phase occurs in the blood samples when the coagulation process is started, and occurs when the initial blood separation has been started.

In one embodiment, the predefined pattern indicates that the amplitude of the signal has reached a substantially steady state over time. In some cases of blood separation in accordance with the invention, physical properties of the blood sample may be in such a way that the amount of fibrin in the liquid or plasma may not be enough for the blood sample to start the phase of fibrin compression. Such a case may occur when a patient is on medication to reduce blood clotting, when the patient has liver diseases that reduce the production of fibrinogen, should the patient have hereditary abnormalities to fibrinogen or other physical factors which the patient may have. Thus, when the fibrinogen has completed its polymerisation, the amplitude of the optical signal may be unchanged over time, which indicates that the process is completed and that the fibrin compression stage will not commence. Thus it is possible to halt the centrifugation at this point in time.

In one embodiment, the predefined pattern indicates that at least the fibrin compression phase of the blood sample is started. For the production of a fibrin based blood product it may be advantageous that the fibrin compression phase of the blood centrifugation is started during centrifugation. The fibrin compression phase ensures that the specific components of the whole blood, such as leukocytes (white blood cells) and thrombocytes (platelets) are compressed in such a way that the components adhere to the fibrin. Thus, in order to ensure that the centrifugation process is continued until the fibrin compression phase commences the predefined pattern should indicate when the compression phase is started in order to allow the controller to be configured to recognize that specific part of the pattern in order to prepare for the discontinuation of the centrifugation process.

In another embodiment, the centrifugal force can be reduced when the erythrocytes have been separated from the plasma, but before the leucocytes and platelets have been separated from the plasma. The reduction of the centrifugal force may leave the leucocytes and the platelets within the plasma during polymerisation of the fibrin phase and may thereby be surrounded by fibrin after polymerisation, and may thus be embedded along with the fibrin in the plasma. Thus, when a compression of the fibrin may be performed, the leucocytes and the platelets may be intertwined with the fibrin layer. The optical signature of the plasma during centrifugation, where the plasma comprises both leucocytes platelets in the plasma, is similar to the signature of the optical signal where leucocytes and platelets have been separated, where the difference is that the plasma is less translucent prior to fibrin polymerisation. During polymerisation of the fibrin, the optical signature follows a similar pattern, where the translucency of the plasma decreases gradually during the polymerisation of the fibrin. In one embodiment of the invention, the centrifuge may comprise at least two optical transmitters and two optical receivers. By introducing a higher number of optical transmitters and optical receivers it is possible to transmit more than one optical signal through the blood sample container, increasing the reliability of the amplitude measurements, as a second signal may provide a redundancy to the amplitude measurements. Thus, the controller may be configured to monitor the amplitude of both signals over time during the centrifugation and where the predefined pattern may be applied to both signals, or that a predefined pattern may be constructed for each signal, where the pattern may be constructed on basis of technical experiments applied to both optical signals.

In one embodiment of the invention, the two optical transmitters may be adapted to transmit an optical signal into two different parts of the receptacle and/or the blood sample container. By adapting the optical transmitters to transmit an optical signal through different parts of the container, the optical signals may be utilized to measure the different phases of the blood fractionation at different positions. Thus, if one of the optical measurements shows a certain tendency, indicating at which stage the blood fractionation is at, while the other does not, it may indicate that the phase is not completed in the entire container, but is only partly completed. Thus, the second measurement may be used to supplement the first measurement in order to ensure that the controller is capable of recognizing the desired phase based on the pattern of the two amplitude measurements.

In one embodiment of the invention, the two optical transmitters may be adapted to transmit an optical signal through a central longitudinal axis of the receptacle and/or the blood sample container, where a first optical signal is adapted to pass through first part of the receptacle and/or the blood sample container and the second optical signal is adapted to pass through a part that is distal to the first part of the receptacle and/or the blood sample container. Thus the optical signals are adapted to measure the translucency of the content of the container at two or more different heights of the container. Thus, as the phases of the blood fractionation occur in the direction of the centrifugal force, i.e. in parallel to the longitudinal axis of the container and/or the receptacle, each optical signal may be capable of registering the phases at different stages. This may be seen i.e. during the fibrin compression phase, in that the fibrin in the plasma is pushed downwards in the container, and the plasma in the top of the container would thereby earlier become more translucent than the plasma in a more distal part of the container. Thus, the amplitude of the two optical signals could therefore be utilised to ensure that the controller is capable of more reliably register which phase the blood sample is in at any specific time during the centrifugation.

In one embodiment of the invention, the receptacle may comprise a through-going opening allowing the optical signal to pass through the receptacle in a radial direction. In a number of centrifuges, the rotor is provided with a number of receptacles to receive a container that is to be centrifuged. As the centrifugal force is a substantial force, it may be advantageous that the receptacles are adapted to enclose at least the bottom part of the container, in order to ensure that the container cannot escape the receptacle during centrifugation in a sideward movement or in a movement that is parallel to the centrifugal force (perpendicular to the fixed axis). Thus, the receptacle may be formed in such a way that the receptacle covers the container or at least parts of the container, where the optical signal may be advantageously passed through. Thus, the receptacle may be provided with at least one through going opening, which allows the optical signal to pass through the receptacle, into the container, and pass through the opposite side of the container so that the optical signal may be measured by the optical receiving means. The through going opening may be in any shape, in the form of a hole, slit or any removal of material, where the only requirement is that the optical signal is capable of passing past the wall of the receptacle and measure the liquid sample inside the receptacle and/or the container that is placed inside the receptacle. Alternatively, the throughgoing opening may be covered with a transparent covering ensuring that if there is a leak inside the receptacle, e.g. from the blood sample container, the covering may ensure that the receptacle is fluid and/or liquid tight, and the leak does not transfer from the receptacle and into the inner volume of the centrifuge.

Alternatively, the receptacle may be formed in such a way that it provides an optical pathway from one side of the receptacle to the other, allowing an optical signal to pass through its inner volume. This may be achieved by forming the receptacle in a transparent material, such as a transparent polymer, glass or other types of suitable materials.

The invention also relates to a method of centrifuging a blood sample comprising the steps of: providing a centrifuge comprising a rotor having a rotational axis, at least one receptacle for a blood sample container having a gravitational axis, controller means for controlling the rotational speed of the rotor, optical transmitter for transmitting an optical signal, optical receiver for registering the amplitude of the optical signal; placing a blood sample container inside the receptacle, where the blood sample container comprises a top end and a bottom end and has a central axis, where the gravitational axis of the receptacle is substantially parallel to the central axis of the blood sample container; starting the centrifugal process where the gravitational axis of the receptacle is at an angle to the rotational axis of the centrifuge and where the centrifugal force extends in a direction that first intersects the top end and subsequently the bottom end of the container; transmitting the optical signal through the blood sample container in a direction that is at an angle to the gravitational axis of the receptacle, where the optical signal is transmitted through an upper phase and/or the plasma of the blood sample; registering the amplitude of the optical signal; discontinuing the centrifugal process when the amplitude of the optical signal over time has fulfilled a predefined pattern indicating that at least the fibrin polymerisation phase of the blood plasma is started.

This means that if a blood sample is centrifuged over a period of time, and an optical signal is transmitted into the blood sample it is possible to measure the amplitude of the signal and based on the measurement over time the measurement indicates which state of blood fractioning the blood sample is at any given time. The measurements indicate a degree of transparency of the blood sample or the lack thereof, where the comparison of amplitude measurement over time indicates whether the blood sample is getting more or less transparent, or if the amplitude measurement is in a steady state over a given time.

Thus, as discussed above in relation to the disclosure of the centrifuge in accordance with the invention, the method may be used to predict or recognize when the blood sample has reached its desired state, e.g. when the fibrin compression phase is reached during centrifugation.

The top end of the blood sample container may have an opening that may be closed or a lid to be closed, ensuring that the blood sample container is hermetically closed to the environment after the blood sample has been introduced into the container. The bottom end of the container may be seen as the part of the container that is adapted to receive the parts of the blood sample that are dense, i.e. the parts of the blood sample that sink towards the bottom during centrifugation. When the centrifuge is started, it is preferred that the blood sample container is orientated during the centrifugation in such a way that the centrifugal force travels from the top end of the container towards the bottom end, so that the fractionation of the blood sample occurs in such a way that the erythrocytes sink towards the bottom of the container, the buffy coat gathers above the erythrocytes and the blood plasma is positioned above the buffy coat. Thus, the centrifugal force pushes the more dense particles in the blood sample towards the bottom. Thus, when the blood sample is positioned in accordance with the method, the plasma will always be in a part of the blood sample container that is above the bottom end of the container, and most likely in an upper part of the container, when the container is filled with a blood sample.

Thus, by transmitting an optical signal through the part of the blood sample container where the plasma will appear during fractionation, it is possible to measure the translucency of the plasma during centrifugation.

The centrifuge may be of the kind where the receptacle may be adapted to move from a position where the gravitational axis is substantially parallel to the rotational axis of the centrifuge to a position that is substantially perpendicular to the rotational axis of the centrifuge. The centrifuge may thus be a bucket centrifuge having a swinging bucket (receptacle) or may be a fixed angled centrifuge, where the bucket (receptacle) may be fixed at a certain angle relative to the rotational axis of the centrifuge.

In accordance with the invention, the centrifugal process may be varied prior to the discontinuation of centrifugal process. Thus, the speed of centrifugation may be reduced when the erythrocytes have been separated from the plasma, where the process may be continued at a lower RPM (speed) until it has been established that the fibrin is polymerized. When the fibrin has been polymerized the RPM (speed) may be increased in order to provide a compacting effect of the fibrin. Thus, prior to discontinuation, the amplitude of the optical signal may be utilized to change the speed of centrifugation, and when the fibrin polymerisation has been completed and/or the fibrin compression has been completed, the centrifugation process may be discontinued. The angle of the receptacle in relation to the rotational axis of the centrifuge may be between 30° and 90°. It has been shown that a preferred method of centrifuging may be where the receptacle is at a 90° angle relative to the rotational axis, or where it is substantially perpendicular to the rotational axis. Some centrifuges may have a receptacle where the receptacle is at a fixed angle, where the angle may be anywhere between 30° and 90°.

In one embodiment, the predefined pattern may comprise an amplitude measurement that is substantially unchanged over time which triggers the discontinuing of the centrifugal process. During blood fractioning of a blood sample, the blood sample may go through at least four phases under the preconception that the blood sample is centrifuged for an unlimited amount of time. The phases may be seen as: separation of blood (plasma, erythrocytes, leucocytes, platelets), fibrin polymerisation, fibrin compression and clearing of other plasma components. When the blood sample has been centrifuged for enough time so that the blood sample is in the phase of clearing other plasma components, the amplitude of the signal increases until a point where the other components in the plasma have been forced out of the plasma. When the components are out of the plasma, the amplitude of the optical signal becomes substantially stable, i.e. where it does not change significantly over time (steady state). Thus, by the time the signal has reached steady state it is known that both the fibrin compression and the clearing of the other plasma components is finished. Thus in order to ensure that the blood sample has been centrifuged enough to at least start the fibrin compression phase, the centrifugation may be stopped when the clearing of the fibrin components is completed, i.e. by discontinuing the centrifugation when the amplitude measurement reaches a steady state.

In one embodiment, the predefined pattern may comprise a first increase in the amplitude of the optical signal. The first increase in amplitude, as defined in the present invention, relates to an increase in amplitude of the optical signal during the fibrin compression phase of the blood fractioning. The increase in amplitude commences when the polymerised fibrin begins to be forced out of the plasma towards the bottom of the container, causing the plasma to become clearer as a consequence. Thus, the first increase in amplitude may be seen as the measurement of an optical signal which is becoming stronger over time during the fibrin compression.

When the first increase in amplitude is registered by the controller it is known from experiments that the fibrin compression phase is started, and the blood product is beginning to take shape as the fibrin is compressed to the thrombocytes and/or the leukocytes allowing the thrombocytes and/or the leukocytes to adhere together with the fibrin. Thus, the first increase in amplitude may be an indicator that the centrifugation may be stopped in order to provide a blood product from the blood sample.

The use of the term "first increase in amplitude" does not indicate the first temporal increase in amplitude, as the first increase in amplitude does not necessarily have to be the first registered increase in amplitude over time. The term first increase only indicates an identification of a certain increase in amplitude, and could be identified with any other means.

In one embodiment, the predefined pattern may further comprise a second increase in amplitude of the optical signal. The second increase in amplitude may precede the first increase in amplitude, and may be seen as an indication that the blood sample is in the blood fractioning phase of the initial separation of blood. The increase in amplitude occurs when the components of the blood are separated and the when the whole blood separates into a clear solution of blood plasma in the upper part of the container. Thus, the increase in amplitude indicates that the optical signal is transferred through a portion of the liquid that is relatively clear. However, the second increase in amplitude must be temporally succeeded by the increase in amplitude in order to indicate that the fibrin compression phase is started inside the container.

In one embodiment, the second increase in amplitude followed by a first decrease in amplitude of the optical signal. The first decrease in amplitude follows the second increase in amplitude and indicates that the fibrin polymerisation is started in the clear blood plasma. The fibrin polymerisation causes the clear blood plasma to become more opaque which causes the amplitude of the optical signal to decrease, as less of the optical signal passes through the contents of the container. This decrease in amplitude can be related to the fibrin density inside the plasma and when the amplitude has reached a predefined level, or the amplitude change rate (increase or decrease) has reached a predefined level, the process may be stopped, as either of the two signals can be used to conclude that enough fibrin has been formed during the centrifugation.

In a temporal view of the amplitude measurement, the first increase in amplitude follows the first decrease in amplitude as the polymerised fibrin is compressed in the fibrin compression stage.

It is to be understood that the controller may be configured in such a way that the controller does not react to the second increase in amplitude or the first decrease in amplitude, by programming it to ignore the patterns or by only commencing the amplitude measurements at a time where the second increase in amplitude is finished. It may be obvious based on the present disclosure of the invention to program the controller in such a way that it reacts at its earliest to the measurements to the first increase in amplitude.

In one embodiment, the predefined pattern may further comprise a third increase in amplitude of the optical signal. The third increase in amplitude may be used to indicate that the blood sample is in the fourth phase of the blood fractioning, i.e. the clearing of other components from the blood plasma. Thus, when the particles in the blood plasma are forced towards the bottom of the container, or raises to the surface of the plasma (e.g. fat and lipids) the plasma becomes even clearer than in the fibrin compression phase, which results in an amplitude measurement where the amplitude increases. The third amplitude increase follows the second amplitude increase, where there may be a short interim measurement where a second decrease in amplitude and/or a relatively slow increase in amplitude precede the third increase in amplitude.

In one embodiment, the centrifugal force applied by the centrifuge to the blood sample is at least 400 G, or more preferably at least 600 G, or more preferably at least 800 G, or more preferably at least 1000 G. The applied centrifugal force may further be The applied centrifugal force is at least 1000, 2000, 3000, 4000, 5000, 6000, 7000, 8000, 9000, 10000, 11000, 12000, 13000, 14000, 15000, 16000, 17000, 18000, 19000 or even 20000 times greater than the gravity force, e.g. g, acting on the whole blood, or the applied centrifugal force is within any interval that can be defined from combinations of the mentioned numbers. The time the centrifugal force is applied for may depend on the amplitude measurement, where the controller stops the centrifugation when the centrifugation has resulted in the desired product. The teachings of the necessary centrifugal force may be found in WO 2010/020254 and/or WO 2012/037942.

In one embodiment, the centrifugation of the blood sample may be restarted and the centrifugation may be continued until the optical signal registers a reduction in amplitude when a floating device inside the blood sample container intersects the optical signal. WO 2012/037942 teaches a container having a floating device, where the floating device is adapted to collect the blood product on one surface. In accordance with the invention, the centrifuge or the method may be used in cooperation with a similar device, where the floating device is released during a second centrifugation. When the floating device is released from the lower part of the container, the floating device travels upwards towards the upper part of the device and onwards towards the top of the device. Thus, the amplitude measurement of the optical signal is capable of registering when the floating device intersects the optical signal, as the amplitude measurement decreases quickly over a short period of time. Thus, when the amplitude decreases quickly, this indicates that the floating device is on its way to the top, and the second centrifugation process may therefore be stopped.

Within the meaning of the present invention, a steady state of the amplitude measurement may be defined as a measurement over time where the amplitude of the signal does not change significantly. I.e. when it appears that the rate of increase or decrease in amplitude is relatively low.

Within the meaning of the present invention, the disclosure of the invention relating to the centrifuge may equally be applied to disclosure relating to the method, and vice versa.

The technical features that are disclosed in relation to the centrifuge according to the invention may be implemented in the method according to the invention, and vice versa.

The optical signal may be obtained in any manner, provided that the optical signal emitted and the optical signal measured is a representation of the contents of the blood sample, and especially a representation of the translucency of the blood sample in specific areas. The purpose of the present invention is to obtain a measurement of the status of blood fractioning, in order to obtain the optimal time to halt the centrifugal process, and to allow the blood product to be obtained.

In one embodiment of the invention, when the blood sample container is being used that is similar to that shown in WO 2012/037942, the centrifuge or the method may be adapted to be restarted after the initial discontinuation, in order to allow the buoyancy device to float towards the top of the container.

BRIEF DESCRIPTION OF DRAWINGS

The invention is explained in detail below with reference to the drawings, in which.

DETAILED DESCRIPTION OF DRAWINGS

Figure 1:
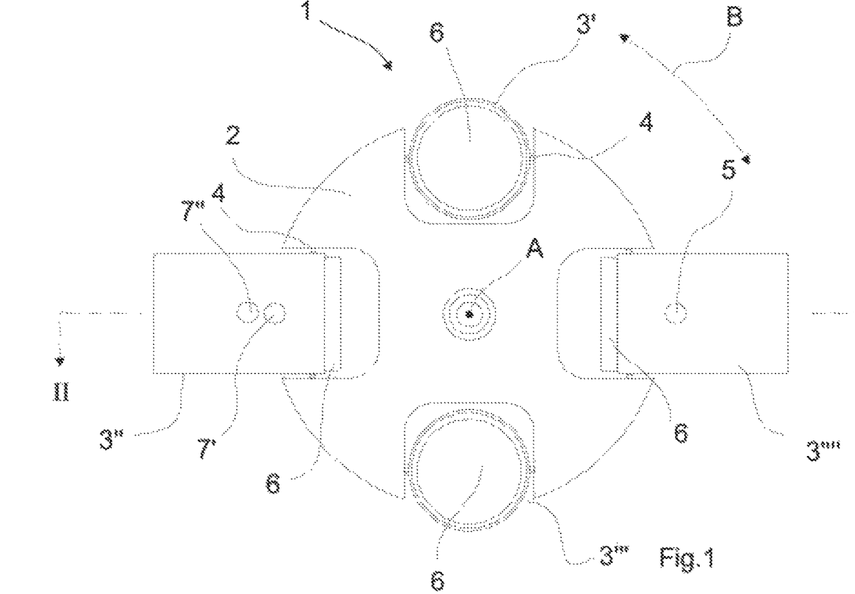
FIG. 1 is a top view of a rotor of a centrifuge in accordance with the invention.

FIG. 1 is a top schematical view of a rotor 2 of a centrifuge 1, where the rotor is capable of spinning across a fixed axis A. The rotor is provided with four receptacles 3', 3", 3''', 3'''' (may be more or less in accordance with the invention), that are attached to the rotor 2. The receptacles are attached to the rotor via a hinge 4, that allows the receptacle to rotate across an axis that is perpendicular to the radial axis of the rotor 2, so that the receptacles are capable of rotating from a vertical position of the receptacle (as shown with 3',3''') when the rotor is stationary to a horizontal position of the receptacle (as shown with 3",3'''') while the rotor rotates along the fixed axis A during centrifugation in one of the directions shown by arrow B.

In the embodiment of a receptacle 3'''', the receptacle 3'''' is provided with a through-going opening 5, that allows access to the inner volume of the receptacle 3, where the inner volume of the receptacle 3 is adapted to receive a container 6 that may be used for holding a blood sample. The through going opening 5 may provide access to the inner volume of the receptacle 3'''' in a radial direction (perpendicular to the longitudinal axis of the receptacle) where an opposite side of the receptacle may be provided with a second through going opening (shown in FIG. 2), allowing a line of sight through the side walls 7 of the receptacle 3'''' via the inner volume of the receptacle 3''''.

Figure 3:
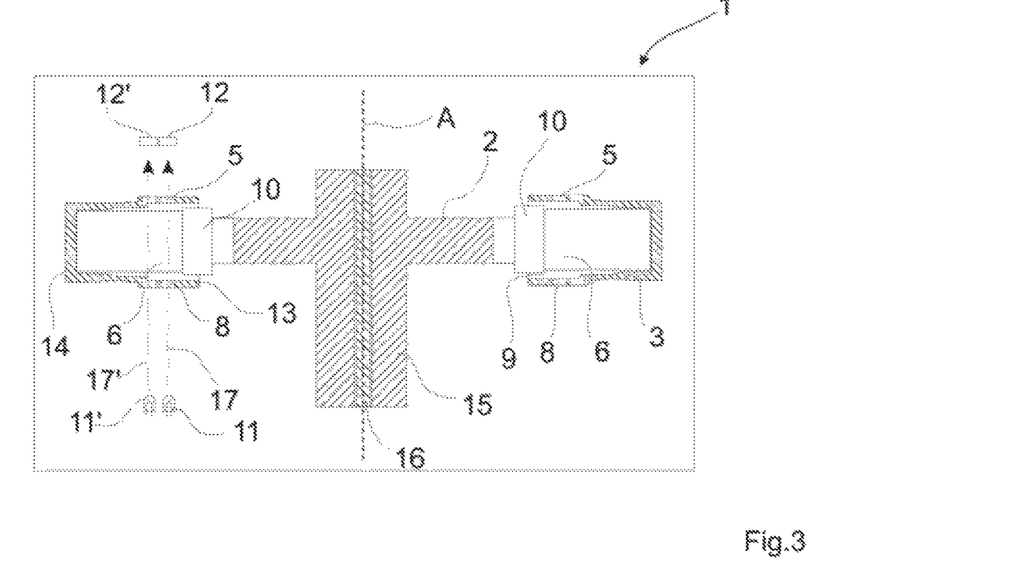
FIG. 3 is a sectional view of a centrifuge using two optical transmitters taken along axis II-II in FIG. 1.

In a different embodiment of a receptacle 3", also shown in FIG. 1, the receptacle 3" may be provided with two through going openings 7', 7", allowing the transmission of two separate optical signals into the inner volume of the receptacle and through matching openings in the opposite side of the receptacle, as shown in FIG. 3.

Figure 2:
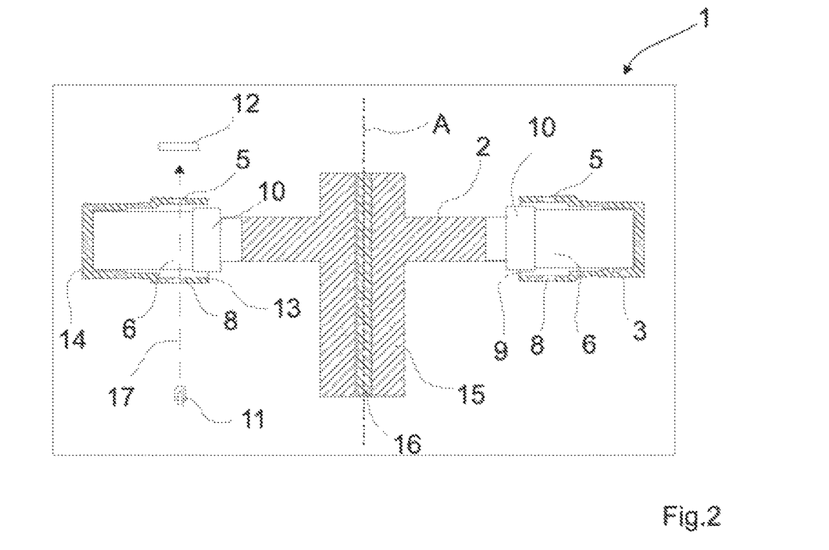
FIG. 2 is a sectional view of a centrifuge using one optical transmitter taken along axis II-II in FIG. 1.

FIG. 2 is a cross-sectional view of a centrifuge using one optical transmitter taken along axis II-II in FIG. 1. The rotor 2 is rotated along a rotor shaft 16, that is parallel to the fixed axis A, where the axle is rotationally attached to a bearing that attaches the rotor shaft 16 to the rotor hub 15. The rotor hub may be driven by a driving means, such as an electrical motor, where the electrical motor may be arranged to provide variable or constant driving force to the rotor hub 15. When the rotor 2 is in motion the receptacles 3 move from their receiving position, a vertical position, as shown in FIG. 1, into an extended position perpendicular to the rotational axis A, so that the proximal end 13 of the receptacle faces in the direction towards the rotational axis while the distal end 14 faces in a direction away from the rotational axis.

The centrifuge 1 is provided with an optical signal source/transmitter 11 that transmits an optical signal in the direction of an optical sensor/receiver 12 that may be positioned in a direction that is vertical to the optical transmitter 11. The optical signal is transmitted into an area of the centrifuge, where the receptacle passes through the optical signal 17. As previously mentioned, the receptacle may be provided with a through-going opening 8 on a side wall of the receptacle 3, allowing the optical signal to enter the inner volume 9 of the receptacle and exit the receptacle 3 through a through-going opening 5 on an opposite side of the side wall of the receptacle 3, so that the optical signal 17 passes through the inner volume 9 of the receptacle 3.

Thus, if a container 6 is filled up with a liquid, such as a blood sample, and closed with a lid 10 and is subsequently positioned inside the inner volume 9 of the receptacle 3, the optical signal 17 intercepts the inner volume of the receptacle where the container 6 has been positioned. By having a container having a side wall that is permeable to optical signals, e.g. by being transparent, the signal 17 will thereby pass through the container 6, and the contents of the container in the area where the signal 17 passes. Thus, when the signal intersects an object that is transparent, the amplitude of the signal, being measured by the sensor/receiver 12 is relatively high, while if the signal intercepts an object that is opaque, the amplitude of the signal will be reduced relative to the amplitude through the clear object.

During centrifugation the optical signal may be transmitted through the receptacle 3 and the container 6 in order to provide continuous measurements of the transparency of the object inside the receptacle during centrifugation. Thus, in the event that the transparency of the object changes over time, such as occurs during blood fractioning, the received signal will reflect the transparency of the object at any given time. By providing a continuous optical measurements of the amplitude of the optical signal it is possible to detect whether or not the contents is getting more transparent, less transparent or is in a steady state.

The positioning of the Optical receivers and/or the optical transmitters may be changed in accordance with the invention, provided that it is ensured that the optical signal is allowed to pass through the liquid, or blood sample, that is to be measured. Thus, the positioning of the transmitters or receivers may be inverted, or that the optical signal passes through the liquid at an angle, is reflected using a mirror, or is otherwise changed in relation to the present embodiment.

FIG. 3 is a sectional view of a centrifuge using two optical transmitters 11, 11' and two optical receivers 12, 12' taken along axis II-II in FIG. 1. In this embodiment, the two optical signals 17, 17' are adapted to pass through the receptacle 3 and/or container 6 at different positions along the direction of the centrifugal force. Thus, it is possible to measure the amplitude of the optical signals 17 at different areas of the receptacle using separate sensors/receivers 12, allowing the controller to utilize two different measurements to assess if the blood fractioning is at an optimal stage during centrifugation. Otherwise the centrifuge shown in FIG. 3 is operated similarly to the centrifuge of FIG. 2, where the output of the signals is disclosed in relation to FIG. 5.

Figure 4:
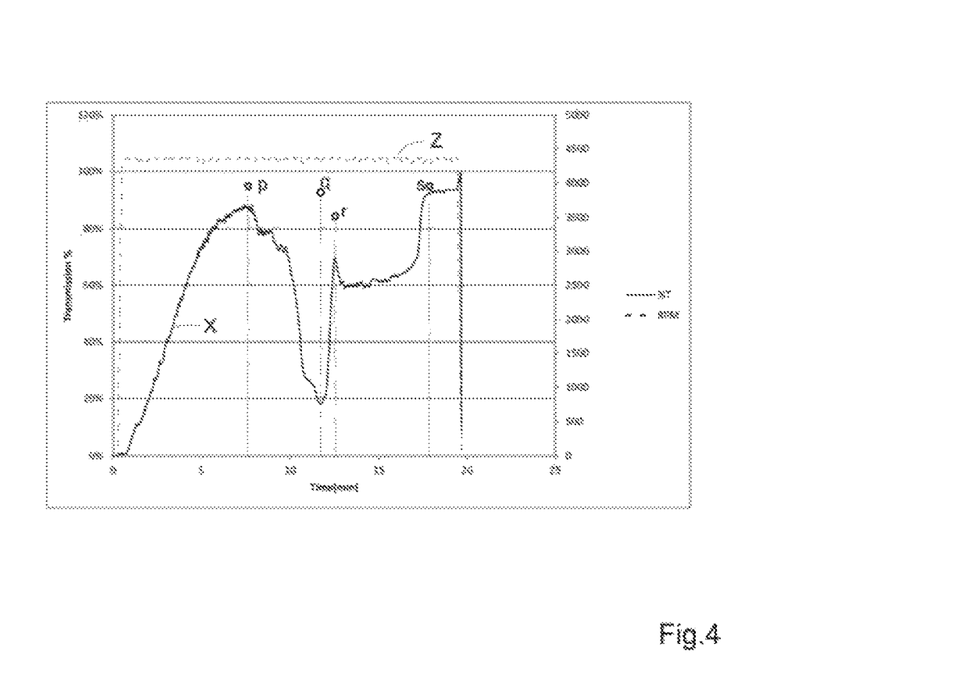
FIG. 4 represents measurement data of a blood fractioning of a blood sample using a centrifuge comprising one optical transmitter and receiver.

FIG. 4 represents measurement data of a blood fractioning of a blood sample using a centrifuge comprising one optical transmitter and receiver, similar to that shown in FIG. 2. The graphical representation in FIG. 4, shows a time scale in minutes on the horizontal axis, a transmission % (optical signal amplitude) scale on the leftmost vertical axis and a RPM (revolutions per minute) scale on the rightmost vertical axis. The data represented in the graph is an optical signal amplitude measurement X and a centrifugation speed Z.

The optical signal was directed towards an upper part of the blood sample container, in order to be in an area where the where the components of the whole blood are pushed downwards in a direction away from the area that is measured. The measured area is an area where the blood plasma appears during centrifugation.

The centrifugation speed was maintained at approximately 4400 RPM from the beginning of the measurement ($\approx 0$ min) and until the discontinuing of the measurement ($\approx 19.7$ min).

In the first period, from 0 min-7.85 min where the end of the period is marked with the line p, the blood sample is being fractioned and is in the separation of blood phase, as discussed earlier. In accordance with the data, the clarity of the measured blood increases, as the thrombocytes, erythrocytes and the leukocytes are pressed towards the lower part of the container, allowing the whole blood/blood plasma to increase in clarity which is represented by the increase in clarity of the data. Thus at the end of the first period, the translucency of the signal has peaked for this period, where the first phase is replaced with the second phase, represented in the second period.

In the second period, 7.85-11.75 min, the fibrinogen in the blood plasma begins to polymerize, causing the blood plasma to be less clear (more opaque), which causes the amplitude of the transmission signal to reduce significantly, by where the amplitude of the signal to decrease from approximately 90% to 20%. When the fibrinogen has polymerized into fibrin, the translucency of the plasma is reduced due to the contents of fibrin in the plasma. The change in amplitude may change from one patient to the other, where fat in the blood sample can reduce the translucency of the plasma and the initial fibrin concentration may have an effect on the measurements. However, blood sample will become more or less translucent during the centrifugation period, and the representation of the translucency in form of the amplitude increase, decrease or steady-state may be important for identifying the phases of blood fractioning.

Figure 6:
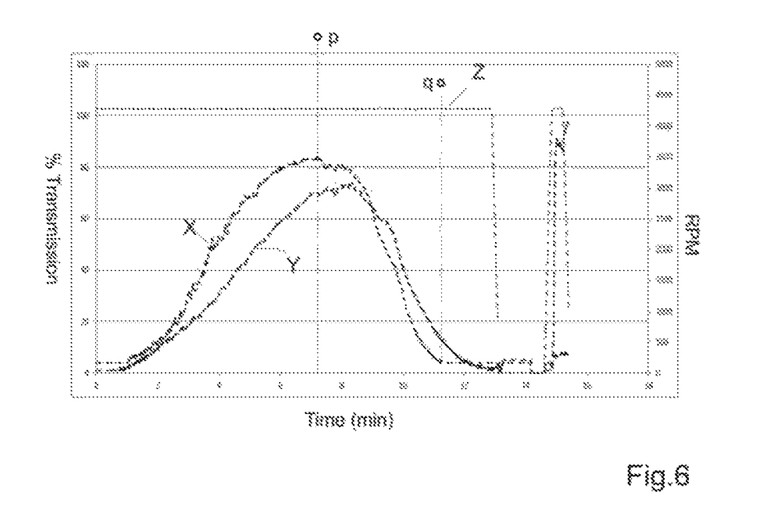
FIG. 6 represents measurement data of blood fractioning of a blood sample, similar to that disclosed in FIG. 4 and represented in FIG. 5, where the blood sample does not commence on the fibrin compression phase.

When this phase of the fibrin polymerization has commenced or is finished the centrifugation process may be halted, especially when the there is a reduced fibrin content in the plasma. Such a situation is shown in FIG. 6, where the fibrin polymerization is not succeeded by the next phase, i.e. the fibrin compression phase.

When the fibrin has been formed in the blood plasma, the fibrin begins to be pushed towards the bottom of the container, and the third phase of fibrin compression is initiated. The third phase initiates at approximately 11.75 min, which is the end of the previous phase and is marked by the line q and where this phase ends at approximately 12.5 min, marked by the line r. In this phase the fibrin is compressed in the lower area of the container and the clarity in the plasma increases rapidly as the fibrin is removed from the plasma.

The fourth phase of the blood fractioning starts at approximately 12.5 min, marked by the line r, and continues until approximately 17.5 min marked by line s in the graph. In this phase the blood plasma is becoming clearer, as some of the remaining components in the blood plasma are being cleared from the plasma as the centrifugal force forces the components towards the lower part of the container or that components rise towards the surface due to density difference. Thus, this phase may be recognized by an increase in amplitude of the transmitted signal as the remaining components gradually move from the plasma.

Subsequent to the fourth phase, the amplitude measurements go into a steady state, where the translucency of the plasma remains substantially constant.

The measurements represented in FIG. 4 are performed on a blood sample from one test subject. It may be seen that each phase of the blood fractioning may be represented by a translucency measurement of the blood sample. However, as there is quite a high variation between one subject to the next in relation to the time it takes to fraction the blood, the signals may be different from one person to the next. The cause for this variation may be physiological, pharmaceutical, physical or have other different causes. However, when fractioning a blood sample that has not been anti-coagulated, and where the blood is capable of coagulating, the phases are similar in most subjects. There may be an exception, where the fibrin concentration in the blood sample is not high enough to allow the fibrin compaction phase to commence. The phases may be recognized using optical measurements in accordance with the present invention, in order to prevent that a blood sample is either centrifuged for an excess amount of time, or alternatively for too short time.

By configuring a controller to recognize the phases using a predefined pattern recognition algorithm or using other means, it is possible to automatically assess what stage the blood sample is at any given time, and stop the centrifugation when the blood sample is in a desired phase.

Figure 5:
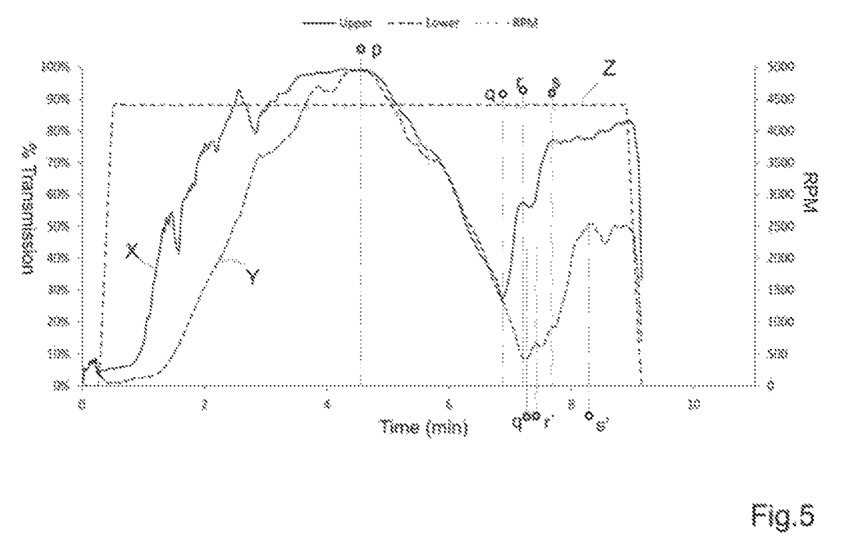
FIG. 5 represents measurement data of a blood fractioning of a blood sample using a centrifuge comprising two optical transmitters and two optical receivers.

FIG. 5 represents measurement data of a blood fractioning of a blood sample using a centrifuge comprising two optical transmitters and two optical receivers, similar to that shown in FIG. 3. The graphical representation in FIG. 5 is similar to that shown in FIG. 4, where X represents data from an optical transmitter/sensor that is positioned in an upper part of a receptacle/container while Y represents data from an optical sensor that is adapted to measure from a lower part of the receptacle/container, and Z represents the centrifugal speed.

In FIG. 5 it possible to see that the data from the upper measurement X shows the exactly same tendencies as the signal represented in FIG. 4, where the difference between this signal an the previous signal is that the phases are completed at a much shorter time, even though the centrifugal forces in both measurements is the same, as the blood sample was centrifuged in the same centrifuge, at the same speed and under the same conditions as the sample of FIG. 4. The end of the first phase, marked by the line p is finished at approximately 4.75 min, where the second phase is concluded at approximately 6.8 min marked by line q, the third phase at 7.2 min, marked by line r, while the fourth phase is finished at 7.7 min, marked by line s.

Thus, the blood sample in FIG. 5 reached point s at an earlier time than the measurement shown in FIG. 4, which means that if the centrifugation would have been continued for a period that is comparable to the time it took to reach the close of the fourth phase marked by the line s in FIG. 4, a considerable amount of excess time would have been used.

The second signal Y, which is positioned at a lower position in the receptacle/container, correlates substantially with the signal X, but appears to be shifted in time. Thus, the signal Y shows the same tendencies as signal X, but is later to indicate the changes in the first phase (up to line p), the second phase where the transparency amplitude continues to a lower amplitude than for the first signal (q'), and where the end of the third (r') and fourth phases (s') are slightly shifted in time relative to the upper signal X.

However, the second signal Y shows the same increases and decreases in amplitude as the first signal, which means that such a signal could be utilized as a redundancy for the pattern recognition, or that the pattern recognition could be configured to discontinue the centrifugation when both signals have fulfilled the predetermined pattern.

FIG. 6 represents measurement data of a blood fractioning of a blood sample using a centrifuge comprising two optical transmitters and two optical receivers, similar to that shown in FIG. 3. In this situation the amplitude of the optical signal X increases until it reaches its peak, where line p intersects signal X, where the initial blood separation occurs and the plasma becomes relatively clear. Subsequently, after point p, the fibrin polymerization starts and the amplitude of the signal reduces until it reaches a low point, where line q intersects signal X. In this situation the subsequent phase of fibrin compression has not commenced, due to the physical properties of the blood sample, and the centrifuge may be stopped, when the signal has reached a steady state, where the fibrin remains in the plasma. Thus, in order to obtain the blood product, it may be enough that the fibrin polymerization phase is started and/or completed, and where the centrifuge is stopped when the fibrin has been polymerized. Thus, in order to obtain the compression of the fibrin, the fibrin may be compressed "manually" using the filter device disclosed in WO 2012/037942, where the filter device floats up in the blood sample, collecting the fibrin, thrombocytes and leukocytes and where it compresses the fibrin as it is raised in the blood sample. Alternatively, the fibrin compression may be done manually.

The specific amplitude or the scale of the measurements shown in FIG. 4, 5 or 6 are not relevant for the present method, as it is the change over time of the amplitude measurement that reflects the changes in translucency of the measured sample.

EXAMPLE

In accordance with the invention, a centrifuge and a method of using the centrifuge in accordance with the following example have been provided.

An Eppendorf centrifuge has been modified where a white LED emitter has been placed in the bottom area of the centrifuge compartment and a light sensor has been placed in the upper area of the centrifuge compartment. A centrifuge cup (receptacle) has been modified where openings have been arranged in the centrifuge cup allowing light to pass through the cup, when the cup is in its extended (horizontal position) from the LED to the light sensor.

The light has been coupled with the rotation of the centrifuge, so that the LED emitter lights up when the openings in the cup are at an angular position where they line up between the LED emitter and the light sensor, so that the light passes through the opening in the bottom, through the inner volume of the cup, and out towards opening in the top, towards the light emitter.

Thus, the signals received from the light sensor are discrete signals which represent the light which passes through the cup during the centrifugal process. Thus, it is not necessary to crop the signals to isolate the relevant portions, as the light was only emitted when the light was capable of passing through the openings of the cup.

The centrifuge was provided with four cups, which were placed in pairs diametrically opposed from each other across the rotational axis, so that the angle between the four cups was about 90°, and the centrifuge was therefore balanced across the rotational axis of the centrifuge.

The invention claimed is:
1. A method of centrifuging a blood sample to form a blood product, the method comprising the steps of:
providing a centrifuge comprising a rotor having a rotational axis, at least one receptacle for a blood sample container having a gravitational axis, controller means for controlling the rotational speed of the rotor, optical transmitter for transmitting an optical signal, optical receiver for registering an amplitude of the optical signal,
placing a blood sample container inside the receptacle, where the blood sample container comprises a top end and a bottom end and has a central axis, where a gravitational axis of the receptacle is substantially parallel to the central axis of the blood sample container,
starting the centrifugal process, where the gravitational axis of the receptacle is at an angle to the rotational axis of the centrifuge and where a centrifugal force extends in a direction that first intersects the top end and subsequently the bottom end of the container,
transmitting the optical signal towards the blood sample container in a direction that is at an angle to the gravitational axis of the receptacle, where the optical signal passes through a wall of a single blood sample container to an opposite wall of the single blood sample container and is transmitted through an upper phase and/or a plasma of the blood sample at an angle of about 30 degrees up to about 90 degrees relative to the gravitational axis of the receptacle, wherein an optical signal path of the optical signal passes from the optical transmitter through no more than one blood sample container and then to the optical receiver, registering the amplitude of the optical signal on a side of the receptacle opposite to a source of the optical signal, where the amplitude of the optical signal reflects a translucency of an upper phase and/or plasma of the blood sample in the blood sample container and wherein the amplitude of the optical signal over time indicates a blood product formation in the blood sample container, and discontinuing the centrifugal process when the amplitude of the optical signal over time has fulfilled a predefined pattern, indicating that at least a fibrin polymerisation phase of the blood plasma is started.

2. A method of centrifuging a blood sample in accordance with claim 1, wherein the predefined pattern indicates that at least a fibrin compression phase of the blood sample is started.

3. A method of centrifuging a blood sample in accordance with claim 1, wherein the predefined pattern comprises an amplitude measurement that is substantially unchanged over time which triggers the discontinuing of the centrifugal process.

4. A method of centrifuging a blood sample in accordance with claim 1, wherein the predefined pattern comprises a first increase in the amplitude of the optical signal.

5. A method of centrifuging a blood sample in accordance with claim 4, wherein the predefined pattern further comprises a second increase in amplitude of the optical signal.

6. A method of centrifuging a blood sample in accordance with claim 5, wherein second increase in amplitude is followed by a decrease in amplitude of the optical signal.

7. A method of centrifuging a blood sample in accordance with claim 5, wherein the predefined pattern further comprises a third increase in amplitude of the optical signal.

8. A method of centrifuging a blood sample in accordance with claim 1, wherein the centrifugation of the blood sample is restarted and the centrifugation is continued until the optical signal registers a reduction in amplitude when a floating device inside the blood sample container intersects the optical signal.

9. A centrifuge for blood product formation, the centrifuge comprising
a rotor having a rotational axis,
at least one receptacle for a blood sample container having a gravitational axis, where the receptacle comprises a top end for receiving the blood sample container and a bottom end for holding the blood sample container where the receptacle is at an angle to the rotational axis of the centrifuge, where the centrifugal force extends from the top end of the receptacle towards the bottom end of the receptacle,
controller means for controlling the rotational speed of the rotor,
at least one optical transmitter for transmitting an optical signal through a wall of the blood sample container to an opposite wall of the blood sample container in a direction that is at an angle of about 30 degrees up to about 90 degrees relative to the gravitational axis of the receptacle and through an upper portion of the blood sample container,
at least one optical receiver located on a side of the receptacle opposite to the optical transmitter for registering an amplitude of the optical signal, whereby an optical signal path of the optical signal passes from the optical transmitter through no more than one blood sample container and then to the at least one optical receiver,
where the optical receiver detects the amplitude of the optical signal, where the amplitude of the optical signal reflects a translucency of an upper phase and/or a plasma of a blood sample in the blood sample container, whereby the amplitude of the optical signal over time indicates the blood product formation in the blood sample container,
where the controller means is configured to discontinue the rotational movement of the rotor when the amplitude of the optical signal over time has fulfilled a predefined pattern, indicating that at least a fibrin polymerisation phase of the blood plasma is started.

10. A centrifuge in accordance with claim 9, where the centrifuge comprises at least two optical transmitters and two optical receivers.

11. A centrifuge in accordance with claim 10 where the two optical transmitters are adapted to transmit an optical signal into two different upper portions of the receptacle and/or the blood sample container.

12. A centrifuge in accordance with claim 10, where the two optical transmitters are adapted to transmit an optical signal angular to a central longitudinal axis of the receptacle and/or the blood sample container, where a first optical signal is adapted to pass through a first upper portion of the receptacle and/or the blood sample container and the second optical signal is adapted to pass through an upper portion that is distal to the first upper portion of the receptacle and/or the blood sample container.

13. A centrifuge in accordance with claim 12, where the receptacle comprises a through-going opening allowing the optical signal to pass through the receptacle in a radial direction of the receptacle.

14. A centrifuge in accordance with claim 11, where the two optical transmitters are adapted to transmit an optical signal angular to a central longitudinal axis of the receptacle and/or the blood sample container, where a first optical signal is adapted to pass through a first upper portion of the receptacle and/or the blood sample container and the second optical signal is adapted to pass through an upper portion that is distal to the first upper portion of the receptacle and/or the blood sample container.

15. A centrifuge in accordance with claim 14, where the receptacle comprises a through-going opening allowing the optical signal to pass through the receptacle in a radial direction of the receptacle.

16. A method of centrifuging a blood sample in accordance with claim 2, wherein the predefined pattern comprises a first increase in the amplitude of the optical signal.

17. A method of centrifuging a blood sample in accordance with claim 16, wherein the predefined pattern further comprises a second increase in amplitude of the optical signal.

18. A method of centrifuging a blood sample in accordance with claim 17, wherein second increase in amplitude is followed by a decrease in amplitude of the optical signal.

19. A method of centrifuging a blood sample in accordance with claim 18, wherein the predefined pattern further comprises a third increase in amplitude of the optical signal.

* * * * *